Figure 2A:
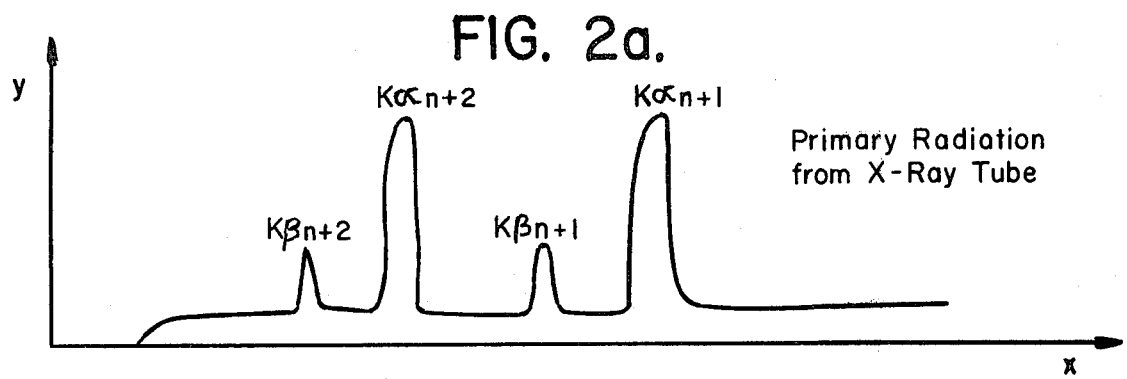

United States Patent [19]

Baecklund

[11] 4,349,738
[45] Sep. 14, 1982

[54] METHOD OF MEASURING THE CONTENT OF GIVEN ELEMENT IN A SAMPLE BY MEANS OF X-RAY RADIATION

[76] Inventor: Nils J. Baecklund, Sunnevik, S-572 00 Oskarshamn, Sweden

[21] Appl. No.: 171,147

[22] Filed: Jul. 22, 1980

[51] Int. Cl.³ .................... G01N 23/20; G21K 1/00
[52] U.S. Cl. .................................... 378/49; 378/83
[58] Field of Search ................................. 250/272

[56] References Cited

U.S. PATENT DOCUMENTS 3,114,832 12/1963 Alvarez .............................. 250/272
3,525,863 8/1970 Constantine et al. ............. 250/272

Primary Examiner—Alfred E. Smith
Assistant Examiner—T. N. Grigsby

[57] ABSTRACT

A method of measuring the content of a given element in a sample by means of X-ray radiation. The sample is first irradiated with primary radiation of a given wave length, to excite first composite fluorescent radiation from the sample whose content of said element is to be determined. Subsequent hereto the sample is then irradiated with primary radiation having a shorter wave length than the first mentioned radiation, to excite a second fluorescent radiation from said sample. The magnitude of the first fluorescent radiation is then subtracted from the magnitude of the second fluorescent radiation, whereat the difference therebetween constitutes the intensity of fluorescence radiation of the shortest wave length which can be excited by the primary radiation having the shorter wave length.

1 Claim, 5 Drawing Figures

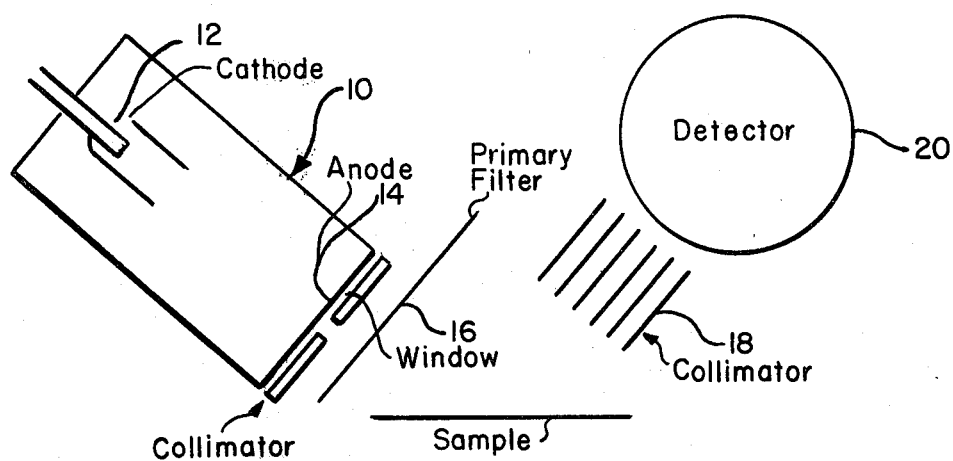

METHOD OF MEASURING THE CONTENT OF GIVEN ELEMENT IN A SAMPLE BY MEANS OF X-RAY RADIATION

The present invention relates to a method of measuring the amount of a given element in a sample by means of X-ray radiation in a portable analysing device.

When monochromatic X-ray radiation falls on a sample whose content of a given element is to be measured, only those X-ray lines in the sample whose wave length is longer than the wave length of the incident X-ray radiation will fluoresce. Because of this the excitation of heavy elements from which it is difficult to separate radiation using conventional filter techniques is generally avoided.

It is known that wavelength resolution or separation can be effected with a flat crystal and a collimator, or with a curved crystal. The fluorescence radiation is wasted in these two methods, however, since about only one part per million of the radiation reaches the detector.

Although germanium detectors can provide satisfactory wavelength resolution, they must be cooled with liquid air in order to function satisfactorily. This renders such detectors unsuitable for use in portable apparatuses.

A change of filter in the fluorescence radiation provides good resolution and high intensity, but is limited by the fact that arbitrary absorption discontinuities or edges are not available and by the fact that, for practical purposes, it is not possible to produce filters from all basic elements.

An object of the present invention is therefore to provide an improved method of the kind described in the introduction, which can be carried out in a portable analysis apparatus.

Accordingly this invention consists in a method of measuring the content of a given element in a sample by means of X-ray radiation, by determining the intensity of the X-ray fluorescence radiation of said element, comprising irradiating the sample with primary radiation containing wavelengths which are shorter than the absorption edges or discontinuities of those elements in the sample which may have a disturbing influence but longer than the absorption edge of the element to be measured, thereby to excite from the sample a first composite fluorescence radiation; measuring said first composite radiation; irradiating said sample with primary radiation which includes at least wavelengths which are shorter than said absorption edge or discontinuity of the element whose quantity is to be measured, thereby to excite from said sample a second composite fluorescence radiation; measuring the intensity of said second composite radiation; subtracting the intensity of the first composite radiation from the intensity of the second composite radiation, and calculating the difference in intensity therebetween, whereat the intensities or the duration of said primary radiations are preselected in a manner such that there is obtained from the sample with both radiations the same fluorescence intensity for an element having absorption edges of longer wavelength than the element whose amount in said sample is to be determined.

It will be understood that the method is dependent on the selected wavelength of the primary radiation. The wavelength of the primary radiation of shorter wavelength may be shorter than the absorption edge or discontinuity by the least possible amount permitted by nature, while the wavelength of the primary radiation of longer wavelength may be longer than said absorption edge of discontinuity by the least possible amount permitted by nature. Thus, there may be any, unspecified difference between the two wavelengths, although the difference between the shorter wavelength and the absorption edge and the longer wavelength and said edge shall be the smallest possible in nature.

IN THE DRAWINGS

Figure 2B:
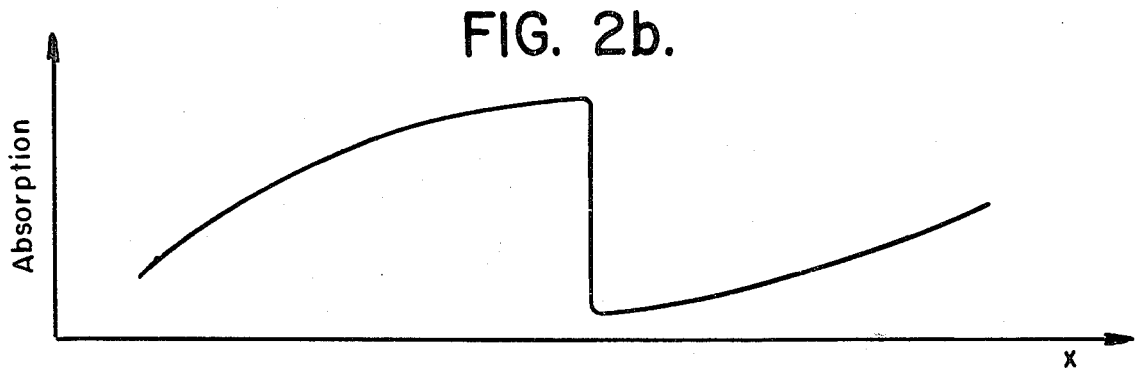
Figure 2C:
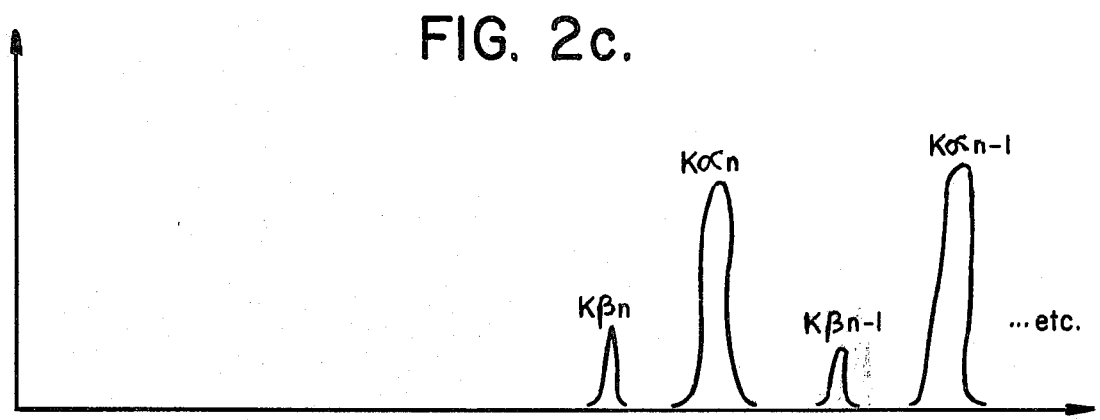
Figure 2D:
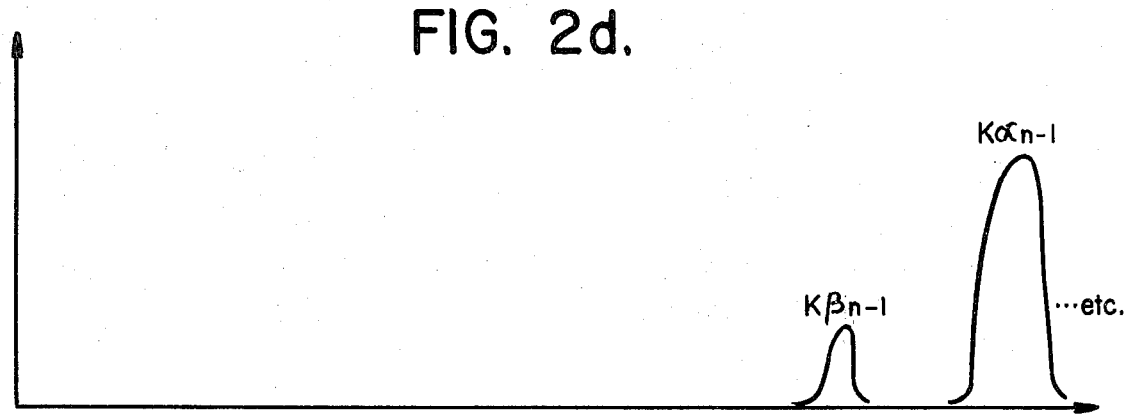

FIG. 1 is schematic showing the apparatus for carrying out the present invention and, FIGS. 2a–2d is a graphic representation of the irradiation waves and the fluorescence waves.

According to the present invention, the primary radiation of longer wavelength is monochromatic radiation of wavelength $\lambda$, and the primary radiation of said shorter wavelength is a combined radiation of wavelength $\lambda$ and $\lambda - 3$, in which d is the difference in wavelength between said shorter and said longer wavelengths.

The method according to the invention can be carried out as seen in FIG. 1 by means of an X-ray tube 10 having a cathode 12 and an anode 14 comprising a mixture of two suitable basic elements, a so-called mixer anode. Alternatively there may be used two separate X-ray tubes, or a tube having two separate anodes. The sample is in a first step irradiated with a first primary radiation of said longer wavelength. If there is used an X-ray tube having a mixer-anode, the X-ray radiation is first caused to pass through a filter 16 for damping radiation of the shorter wavelength. The intensity of the fluorescence resulting from the primary radiation of longer wavelength is passed through a collemeter 18 then measured by detector 20. The sample is in a second step then irradiated with a second primary radiation of both said wavelengths, and the collective, fluorescence intensity measured, which latter intensity now also includes intensities from shorter wavelengths than in the first measuring operation. The collected fluorescence intensity resulting from the primary radiation of longer wavelength is then subtracted from the collected fluorescence intensity resulting from the irradiation with radiation of both short and longer wavelengths. The difference obtained therewith is the fluorescence intensity of the shortest wavelength which can be excited by the primary radiation of said shorter wavelength.

In FIG. 2 the radiation and fluorescence wave forms are graphically depicted. In FIG. 2a, the primary radiation of steps 1 and 2 are shown. FIG. 2b shows the radiation as dampened by the filter. FIG. 2c is the fluorescence from the sample when irradiated without filter, and FIG. 2d is the fluorescence from the sample when the irradiation is filtered.

When carrying out the method according to the invention, it is important that the intensity of the primary radiation is pre-adjusted in a manner to obtain the same fluorescence intensity for an element in the longwave range with both primary radiations.

What I claim is:

1. A method of determining the content of a given element in a sample by means of X-ray radiation, by determining the intensity of the X-ray fluorescence radiation of said element, comprising the steps of irradiating the sample with primary radiation containing wavelengths which are shorter than the absorption edges or discontinuities of those elements in the sample which may have a disturbing influence but longer than the absorption edge of the element to be determined, thereby to excite from the sample a first composite fluorescence radiation; measuring said first composite radiation; thereafter irradiating said sample with primary radiation which includes at least wavelengths which are shorter than said absorption edge or discontinuity of the element whose quantity is to be measured, thereby to excite from said sample a second composite fluorescence radiation; the primary radiation of said longer wavelength being of a wavelength λ, and the primary radiation of said shorter wavelength being a combined radiation of wavelength λ and λ−d, in which d is the difference in wavelength between said shorter and said longer wavelengths, measuring the intensity of said second composite radiation; subtracting the intensity of the first composite radiation from the intensity of the second composite radiation, and calculating the difference in intensity therebetween.

* * * * *